United States Patent [19]

Suzuki et al.

[11] 4,177,112

[45] Dec. 4, 1979

[54] OXYGEN CONCENTRATION DETECTOR AND METHOD OF USE THEREOF

[75] Inventors: Masatosi Suzuki, Kariya; Kazuya Soda, Takahama; Yasuo Nakamura, Anjo, all of Japan

[73] Assignee: Nippondenso Co., Ltd., Kariya, Japan

[21] Appl. No.: 890,903

[22] Filed: Mar. 27, 1978

[51] Int. Cl.$^2$ .................................................. G01N 27/58
[52] U.S. Cl. .................................. 204/1 T; 204/195 S
[58] Field of Search ............. 204/195 S, 1 S; 60/276; 123/119 E, 119 EC; 23/254 E; 422/98

[56]  References Cited

U.S. PATENT DOCUMENTS

| 4,019,974 | 4/1977 | Weyl et al. | 204/195 S |
| 4,021,326 | 5/1977 | Pollner et al. | 204/195 S |
| 4,097,353 | 6/1978 | Kishida et al. | 204/195 S |

Primary Examiner—G. L. Kaplan
Attorney, Agent, or Firm—Cushman, Darby & Cushman

[57]  ABSTRACT

An oxygen concentration detector comprises an oxygen concentration sensor made of an oxygen ion conductive metal oxide which produces an electromotive force in accordance with a difference between an oxygen concentration in gas components of a gas under test and an oxygen concentration in a reference gas, an electrode formed on a surface of the oxygen concentration sensor which is to be exposed to the gas under test and an electrode formed on a surface of the oxygen concentration sensor which is to be exposed to the reference gas so that the electromotive force produced by the oxygen concentration sensor is taken across the electrodes, a first porous coating of a refractory metal oxide formed on the surface of the electrode which is to be exposed to the gas under test, said first coating having a number of pores through which the gas under test can pass, and a second porous coating of a refractory metal oxide formed on the surface of the first coating, said second coating having a number of pores which are larger than the pores of the first coating.

9 Claims, 3 Drawing Figures

OXYGEN CONCENTRATION DETECTOR AND METHOD OF USE THEREOF

The present invention relates to an oxygen concentration detector for detecting an oxygen concentration in gas components of a gas under test such as exhaust gas from an automobile.

A prior art oxygen concentration detector of this type comprises an oxygen concentration sensor made of an oxygen ion conductive metal oxide which may be a solid solution of $ZrO_2$ - $CaO$ and electrodes made of conductive material such as platinum (Pt) formed on the side of the gas under test and the side of a reference gas (atmosphere) of the oxygen concentration sensor. A coating of a refractory metal oxide having pores through which the gas under test can pass is formed on the electrode on the side of the gas under test in order to protect that electrode.

In the prior art detector, when it is exposed to the gas under test (such as exhaust gas of the automobile of a high temperature over a long period of time, the coating is apt to be peeled off from the electrode of the oxygen concentration sensor on the side of the gas under test because of a difference between a thermal expansion of the electrode and a thermal expansion of the coating. Although the coating functions to prevent unburnt material in the gas under test (such as phosphorus, lead, oil) from depositing on the surface of the electrode to prevent the deterioration of the characteristics of the detector due to the deterioration of the electrode, if the pores of the coating are too fine, the pores of the coating are clogged by the deposition of a small amount of unburnt material to the coating so that the gas under test cannot fully contact with the electrode and the electromotive force characteristic of the detector is unstable, which prevents the precise detection of the oxygen concentration. On the other hand, if the pores of the coating are too coarse (large), the protection of the electrode is not attained. It is very difficult to form the coating to overcome both the drawbacks simultaneously.

It is an object of the present invention to provide an oxygen concentration detector which has a long durability and good and stable characteristics.

According to the present invention, a first coating of a refractory metal oxide having a number of pores through which the gas under test can pass is formed on the surface of the electrode mounted on the side of the oxygen concentration sensor which is to be exposed to the gas under test, and a second coating of a refractory metal oxide having a number of pores which are larger than the pores of the first coating is formed on the surface of the first coating. According to the above structure, the difference between the thermal expansions of the electrode and the first coating formed on the surface of the electrode is reduced by the second porous coating at the outermost layer, and even if the pores of the first coating are fine, the unburnt material in the gas under test deposit to the second coating and hence does not substantially deposit to the first coating so that the first coating is not clogged and the unburnt material does not substantially deposit on the electrode surface. Although much unburnt material may deposit on the second coating, it is not readily clogged because it has coarse pores. Thus, the gas under test can pass through the second coating and the first coating to contact with the electrode surface. As a result, the instability of the electromotive force characteristic of the detector can be prevented and hence the oxygen concentration detector having a high durability and good and stable characteristics can be provided.

Those and other objects, features and advantages of the present invention will be apparent from the following description of the preferred embodiments of the invention, when taken in conjunction with the accompanying drawings, in which.

Figure 1:
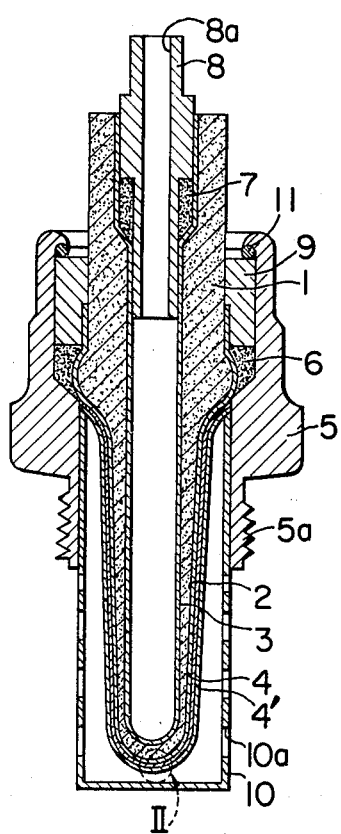
FIG. 1 is a sectional view illustrating one embodiment of a detector of the present invention.
Figure 2:
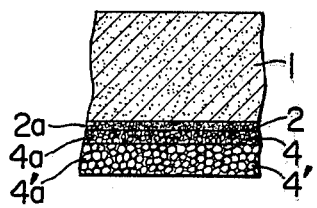
FIG. 2 shows an enlarged system view of a portion II in FIG. 1.

The present invention is now explained in detail with reference to the illustrated embodiment. Referring to FIG. 1, numeral 1 denotes an oxygen sensor made of an oxygen ion conductive metal oxide which may be a solid solution of 70-95 mole % of tetravalent metal oxide such as $ZrO_2$, $ThO_2$ or $CeO_2$ and 30-5 mole % divalent or trivalent metal oxide. In the illustrated embodiment, it is formed by mixing 85 mole % of $ZrO_2$ with 15 mole % of CaO, grinding the mixture and calcing the same, and molding it into a cup-shape and firing it at a temperature of approximately 1600°-1750° C., to form a finely sintered body. The oxygen concentration sensor 1 posseses a property of conducting oxygen ions at an appropriate temperature for the conduction of the oxygen ions, e.g., at 400°-1000° C., when there is a temperature difference between the inner circumference and the outer circumference of the oxygen concentration sensor 1. Platinum (Pt) having a catalytic action is deposited on the outer circumference and the inner circumference of the oxygen concentration sensor 1 by chemical plating, sputtering, vapor deposition or paste application to form a first electrode 2 and a second electrode 3, respectively. Fine grains of $Al_2O_3$ having an average grain size of approximately $10\mu$ are deposited on the surface of the first electrode 2 to the thickness of approximately $30\mu$ by plasma injection-welding to form a first coating 4 having a number of pores. Coarse grains of $Al_2O_3$ having an average grain size of approximately $40\mu$ are deposited on the surface of the first coating 4 to the thickness of approximately $80\mu$ to form a second coating 4' having a number of coarse pores. It is apparent from the comparison of the grain sizes that the pores of the second coating 4' are coarse (larger) than the pores of the first coating 4. This is best shown in FIG. 2, in which numeral 2a denotes the grains of the electrode 2, numeral 4a denotes the grains of the first coating 4, and numeral 4'a denotes the grains of the second coating 4'. Numeral 5 denotes a housing which is used to secure the detector by directly screwing it to an exhaust pipe or the like and which is cylindrical. For the purpose, the housing 5 has a threaded portion 5a. Mounted between the oxygen concentration sensor 1 and the housing 5 are a conductive graphite 6 and an O-ring 9, which are secured by pressing the O-ring downward. Numeral 8 denotes a stem made of stainless steel which is secured by pressing the stem 8 downward at a pressure of 100 Kg while a conductive graphite 7 is interposed between the oxygen concentration sensor 1 and the stem 8. The stem 8 has a center bore 8a to allow the oxygen concentration sensor 1 to be brought into contact with the atmosphere. A caulking ring 11 is placed on the O-ring 9 to secure the entire assembly by calking. The housing 5 is electrically connected to the first electrode 2 through the conductive graphite 6 and the O-ring 9 to constitute one of the output terminals. The stem 8 likewise constitutes the other terminal connected to the second electrode 3 through the conductive graphite 7. Numeral 10 denotes a protective tube to relieve the oxygen concentration sensor 1 from being brought into direct contact with a large amount of exhaust gas to improve the durability of the sensor. The protective tube 10 has a number of pores 10a.

Figure 3:
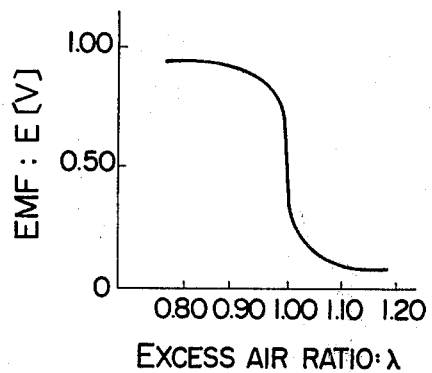
FIG. 3 shows a characteristic curve of an electromotive force of the detector shown in FIG. 1.

The operation of the oxygen concentration detector of the present invention constructed in the manner described above is now explained. The oxygen concentration detector having the structure shown in FIG. 1 may be mounted on the exhaust pipe of an automobile and hence it is exposed to the exhaust gas. An air-fuel ratio of air-fuel mixture before it is burnt in an internal combustion engine relates to concentration of gas components (CO, HC, $O_2$ etc.) in the exhaust gas and the oxygen concentration sensor 1 produces an electromotive force which varies with a difference between an oxygen concentration in the exhaust gas and an oxygen concentration in the atmosphere. The characteristic thereof depicts a Z-curve to an excess air ratio $\lambda$ (which relates to an air-fuel ratio and $\lambda$ of unity corresponds to a stoichiometric air-fuel ratio), and the electromotive force changes abruptly at the point of $\lambda = 1$, as shown in FIG. 3. This abrupt change is due to the catalytic actions of the first and second electrodes 2 and 3. When a three-way catalyst which purifies the $NO_x$, CO and HC components in the exhaust gas simultaneously is used, the amount of $NO_x$ is less on the richer side of the air-fuel ratio and the amounts of HC and CO are less on the leaner side of the air-fuel ratio. It is near the stoichiometric ratio ($\lambda = 1$) that the amount of those three components is minimum. Therefore, a feedback system for the internal combustion engine which manages the electromotive force E of the oxygen concentration detector at the point of $\lambda = 1$ to control the air-fuel ratio can attain the purification of the exhaust gas in a very efficient manner.

Test samples of the first and second coatings 4 and 4' having different grain sizes and thicknesses were prepared and the responses thereof after the durability test were measured. The results are shown below.

Table 1

| 2nd Coating Grain Size | 1st Coating Grain Size Finer than 400 mesh (37 $\mu$) | Finer than 325 mesh (44 $\mu$) | Finer than 270 mesh (53 $\mu$) | Finer than 250 mesh (63 $\mu$) |
| --- | --- | --- | --- | --- |
| Coarser than 270 mesh (53 $\mu$) and finer than 100 mesh | A | B | C | D |
| Coarser than 250 mesh (63 $\mu$) and finer than 100 mesh | E | F | G | H |
| Coarser than 200 mesh (74 $\mu$) and finer than 100 mesh | I | J | K | L |
| Coarser than 170 mesh (88 $\mu$) and finer than 100 mesh | M | N | O | P |

The Table 1 above shows the combinations of the test samples of the first and second coatings having different grain sizes. In the Table 1, the horizontal line shows the grain sizes of the first coating which change in four steps from 400 mesh to 250 mesh, and the vertical column shows the grain sizes of the second coating which change in four steps from 270 mesh to 170 mesh, and sixteen different combinations of those grain sizes are shown as the test samples A to P.

Table 2

| Durability Test Time (Hrs) Sample | Response Time (m sec) | | | | | |
| --- | --- | --- | --- | --- | --- | --- |
| | Initial | 200 | 400 | 600 | 800 | 1000 |
| A | 195 | 190 | 190 | 185 | 190 | 195 |
| B | 180 | 180 | 175 | 180 | 185 | 190 |
| C | 160 | 155 | 160 | 170 | 175 | 180 |
| D | 140 | 130 | 140 | 155 | 165 | 175 |
| E | 185 | 180 | 175 | 180 | 180 | 190 |
| F | 170 | 170 | 165 | 175 | 180 | 185 |
| G | 155 | 150 | 150 | 160 | 170 | 185 |
| H | 140 | 130 | 140 | 155 | 170 | 180 |
| I | 175 | 175 | 170 | 180 | 185 | 190 |
| J | 155 | 155 | 150 | 165 | 175 | 185 |
| K | 140 | 135 | 145 | 155 | 165 | 175 |
| L | 125 | 110 | 115 | 130 | 145 | 160 |
| M | 165 | 165 | 160 | 165 | 170 | 180 |
| N | 140 | 130 | 140 | 155 | 165 | 175 |
| O | 120 | 110 | 120 | 140 | 155 | 170 |
| P | 100 | 95 | 100 | 120 | 140 | 160 |

Table 2 above shows the response times of the sixteen test samples after the durability test over the respective durability test hours. The thicknesses of the first and second coatings were 50$\mu$, respectively. The target value of the response speed (time) of the test samples was set to not more than 200 m sec, and all of the test samples attained the target value (not more than 200 m sec) as is apparent from the Table 2.

Using the test sample F, the response times were measured in the like manner for different thicknesses of the first and second coatings. The results are shown in Table 3.

Table 3

| Sample | Grain Size ($\mu$) | | Response Time (m sec.) | | | | | |
| --- | --- | --- | --- | --- | --- | --- | --- | --- |
| | 1st Coating | 2nd Coating | Initial | 200 Hrs | 400 Hrs | 600 Hrs | 800 Hrs | 1000 Hrs |
| F | 0 | 100 | 90 | 90 | 120 | 180 | 230 | 280 |
| | 20 | 80 | 110 | 110 | 130 | 155 | 175 | 200 |
| | 40 | 60 | 130 | 125 | 140 | 155 | 165 | 180 |
| | 60 | 40 | 165 | 160 | 165 | 170 | 175 | 185 |
| | 80 | 20 | 190 | 185 | 180 | 190 | 190 | 195 |
| | 100 | 0 | 270 | 260 | 250 | 260 | 270 | 280 |

It is apparent from the Table 3 that the target value (not more than 200 m sec) was attained when the thickness of the first and second coatings was 20–80$\mu$.

Using the test sample F, the response times after the durability test were measured in the like manner for different total thicknesses of the first and second coatings from 25$\mu$ to 200$\mu$, with the ratio of the thickness of the first coating to the thickness of the second coating being equal to unity. The results are shown in Table 4.

Table 4

| Sample | Total thickness ($\mu$) | Response Time (m sec.) | | | | | |
|---|---|---|---|---|---|---|---|
| | | Initial | 200 Hrs | 400 Hrs | 600 Hrs | 800 Hrs | 1000 Hrs |
| F | 25 | 110 | 120 | 150 | 175 | 205 | 230 |
| | 50 | 140 | 130 | 145 | 165 | 180 | 195 |
| | 75 | 155 | 155 | 150 | 160 | 175 | 190 |
| | 100 | 170 | 170 | 165 | 175 | 180 | 185 |
| | 125 | 180 | 175 | 175 | 180 | 185 | 190 |
| | 150 | 195 | 190 | 190 | 195 | 195 | 200 |
| | 175 | 220 | 210 | 205 | 215 | 220 | 230 |
| | 200 | 350 | 350 | 340 | 350 | 350 | 360 |

It is seen from the Table 4 that the total thickness which can attain the target value of the response time is from 50 to 150$\mu$.

From the results of various experiments shown above, it is appropriate that the first coating and the second coating have the following grain sizes and the thicknesses:

1st coating grain size: finer than 250 mesh
2nd coating grain size: coarser than 270 mesh and finer than 100 mesh
Ratio of the thickness of the 1st coating to the thickness of the 2nd coating: 20–80:80–20
Total thickness of the 1st and 2nd coatings: 50–150$\mu$ The inventors of the present invention have proven that when the oxygen concentration sensor was made of a solid solution of 90 mole % of zirconium oxide and 10 mole % of yttrium oxide, a sufficient electromotive force characteristic was obtained even for a relatively low temperature (320° C.) exhaust gas.

The present invention is not limited to the illustrated embodiment but various modifications as shown below may be made:

(1) The material of the first coating 4 and the second coating 4' may be a material other than $Al_2O_3$, such as $ZrO_2$, $MgO-Al_2O_3$ or $Cr_2O_3$, or may be a combination of different materials such as $Al_2O_3$ for the first coating 4 and $ZrO_2$ for the second coating 4'.

(2) The material of the first coating 4 may consist of $Al_2O_3$ and Pt, for example.

(3) The coating layers need not be two layers but a multi-layer structure such as three layers or four layers may be used, although the pores of the outer layer must be coarser than those of the inner layer.

(4) The material of the first electrode 2 and the second electrode 3 may be a metal other than Pt, such as Pd, Ag, Au, Ir or Rh or an alloy thereof, or even a metal having no catalytic action when the catalytic action is not required for the electrode.

While the oxygen concentration sensor 1 is shaped into the cup-shape having one end opened and the other end closed in the illustrated embodiment, it may be shaped into a plate-shape or cylinder shape.

Furthermore, the present invention is not limited to the means for sensing the oxygen concentration in the exhaust gas from the internal combustion engine to detect the air-fuel ratio of the air-fuel mixture to be supplied to the internal combustion engine, but it may be used as means for sensing an oxygen concentration in a combustion product exhausted from a combustion mechanism in a blast furnace or boiler to detect an air-fuel ratio of an air-fuel mixture to be supplied to the combustion mechanism (for improving a thermal efficiency of the combustion mechanism, for example).

What is claimed is:

1. In an oxygen concentration detector having an oxygen concentration sensor made of an oxygen ion conductive metal oxide which produces an electromotive force in accordance with the difference between an oxygen concentration in gas components of a gas under test and the oxygen concentration in a reference gas, including a first electrode formed on the side of said oxygen concentration sensor which is to be exposed to the gas under test, and a second electrode formed on the side of said oxygen concentration sensor which is to be exposed to said reference gas so that the electromotive force produced by said oxygen concentration sensor is measured across said first and second electrodes;

the improvement comprising;
(i) a first porous coating of a refractory metal oxide coated on the surface of said first electrode, the grain size of said first porous coating being finer than about 250 mesh and said first porous coating having pores through which the gas under test can pass; and
(ii) a second porous coating of a refractory metal oxide coated on the surface of said first coating, the grain size of said second porous coating being about 250 to about 100 mesh and said second porous coating having pores whose average diameter is larger than that of the pores of said first coating.

2. An oxygen concentration detector according to claim 1, wherein said oxygen ion conductive metal oxide is a solid solution of $ZrO_2$ and a material selected from the group consisting of CaO and $Y_2O_3$.

3. An oxygen concentration detector according to claim 1, wherein said first and second porous coatings are selected from the group consisting of $Al_2O_3$, $ZrO_2$, $MgO-Al_2O_3$ and $Cr_2O_3$.

4. An oxygen concentration detector according to claim 1, wherein the response time of said detector is faster than 200 m sec in use at a normal operating range.

5. An oxygen concentration detector according to claim 1 wherein a ratio of the thickness of said first porous coating to the thickness of said second porous coating is 20–80:80–20.

6. An oxygen concentration detector according to claim 1 wherein total thickness of said first and second porous coatings is approximately 50–150$\mu$. porous 7. An oxygen concentration detector according to claim 1 further comprising a protective member spaced from said second porous coating and arranged to cover said second porour coating, said protective member having a number of pores.

8. A method of detecting the oxygen concentration in the exhaust gas comprising oxygen, phosphorus, lead and oil from an internal combustion engine comprising:
a. exposing to said exhaust gas an oxygen concentration detector having an oxygen concentration sensor of an ion conductive metal oxide producing an electromotive force in accordance with the difference between the gas coponents of said exhaust gas and the oxygen concentration of a reference gas containing oxygen, said sensor including:
(1) a first electrode formed on the portion of said sensor exposed to the exhaust gas;
(2) a second electrode formed on the portion of said sensor exposed to said reference gas such that in operation an electromotive force is produced across said first and second electrodes;
(3) a first porous coating of a refractory metal oxide coated on the surface of said first electrode, the grain size of said first porous coating being smaller than about 250 mesh and having pores therein through which said exhaust gas passes;

(4) a second porous coating of a refractory metal oxide coated on the surface of said first coating, the grain size of said second coating being about 250 to about 100 mesh and having pores therein whose average diameter is larger than that of the pores of said first coating;

b. exposing said second electrode to said reference gas; and c. measuring the electromotive force produced between said first and second electrodes thereby determining the oxygen concentration in said exhaust gas.

9. A method according to claim 8 wherein said reference gas is air.

* * * * *